United States Patent [19]

Gryaznov et al.

[11] Patent Number: 5,741,643

[45] Date of Patent: Apr. 21, 1998

[54] OLIGONUCLEOTIDE CLAMPS

[75] Inventors: Sergei M. Gryaznov, San Mateo; David H. Lloyd, Daly City, both of Calif.

[73] Assignee: Lynx Therapeutics, Inc., Hayward, Calif.

[21] Appl. No.: 461,271

[22] Filed: Jun. 5, 1995

Related U.S. Application Data

[62] Division of Ser. No. 87,387, Jul. 2, 1993, Pat. No. 5,473,060.
[51] Int. Cl.$^6$ .............................. C12Q 1/68; C12P 19/34; C07H 21/02
[52] U.S. Cl. .............................. 435/6; 435/91.2; 536/23.1
[58] Field of Search .................... 435/6, 91.2; 935/77, 935/78; 536/23.1

[56] References Cited

U.S. PATENT DOCUMENTS

| | | | |
|---|---|---|---|
| 4,599,303 | 7/1986 | Yabusaki et al. | 435/6 |
| 4,739,044 | 4/1988 | Stabinsky | 536/25.3 |
| 4,948,882 | 8/1990 | Ruth | 536/25.32 |
| 4,958,013 | 9/1990 | Letxinger et al. | 514/44 |
| 5,093,232 | 3/1992 | Urdea et al. | 435/6 |
| 5,098,890 | 3/1992 | Gewirtz et al. | 514/44 |
| 5,166,315 | 11/1992 | Summerton et al. | 528/406 |
| 5,473,060 | 12/1995 | Gryaznov et al. | 435/6 |

FOREIGN PATENT DOCUMENTS

| | | |
|---|---|---|
| WO90/00622 | 1/1990 | WIPO. |
| 9010448 | 9/1990 | WIPO. |
| US90/01002 | 9/1990 | WIPO. |
| US91/02224 | 10/1991 | WIPO. |
| US91/06143 | 3/1992 | WIPO. |
| CA92/00423 | 4/1993 | WIPO. |

OTHER PUBLICATIONS

Praseuth et al, PNAS 85:1349–1353 (1988).
Luebke et al, J. Am. Chem. Soc. 111:8733–8735 (1989).
Salunkhe et al. J. Am. Chem. Soc. 114:8768–8772 (1992).
Agrawal, et al., "Site specific functionalization of oligonucleotides for attaching two different reporter groups," *Nuc. Acids Res.* 18:5419–5423 (1990).
Agrawal, et al., "Site–specific functionalization of oligodeoxynucleotides for non–radioactive labelling," *Tetrahedron Lett.* 31:1543–1546 (1990).
Ashley, et al., "Chemical synthesis of oligonucleotide dumbbells," *Biochem.* 30:2927–2933 (1991).
Beal, et al., "Recognition of double helical DNA by alternate strand triple helix formation," *J. Am. Chem. Soc.* 114:4976–4982 (1992).
Blume, et al., "Triple helix formation by purine–rich oligonucleotides targeted to the human diydrofolate reductase promoter," *Nuc. Acids Res.* 20:1777–1784 (1992).
Clontech Laboratories 1989–1990 Catalog (excerpt).
Durand, et al., "Circular dichroism studies of an oligonucleotide containing a hairpin loop made of a hexaethylene glycol chain: conformation and stability," *Nuc. Acids Res.* 18:6353–6359 (1990).

Farooqui, et al., "Effect of structural variations in cholesteryl–conjugated oligonucleotides on inhibitory activity towards HIV–1," *Bioconjugate Chem.* 2:422–426 (1991).
Ferris, et al., "4–cyanomidazole and diimidazole imine: water–soluble condensing agents for the formation of the phosphodiester bond," *Nucleosides & Nucleotides* 8:407–414 (1989).
Fidanza, et al., "Introduction of Reporter Groups at Specific Sites in DNA Containing Phosphorothioate Diesters," *J. Am. Chem. Soc.* 11:9117–9119 (1989).
Francois, et al., "Recognition and cleavage of duplex DNA via triple–helix formation by oligonucleotides covalently linked to a phenathroline–copper chelate," *Proc. Natl. Acad. Sci.* 86:9702–9706 (1989).
Froehler, et al., "Phosphoramidate analogues of DNA: synthesis and thermal stability of heteroduplexes," *Nuc. Acids Res.* 16:4831–4839 (1988).
Giovannangeli, et al., "DNA as a target for triple–helix formation," *J. Am. Chem. Soc.* 113(20):7775–7777 (1991).
Goodchild, "Conjugates of oligonucleotides and modified oligonucleotides: a review of their synthesis and properties," *Bioconjugate Chem.* 1:165–187 (1990).
Gryaznov, et al., "Chemical ligation of oligonucleotides in the presence and absence of a template," *J. Am. Chem. Soc.* 115:3808–3809 (1993).
Gryaznov, et al., "Synthesis and properties of oligonucleotides containing aminodeoxythymidine units," *Nuc. Acids Res.* 20:3403–3409 (1992).
Gryaznov, et al., "Template controlled coupling and recombination of oligonucleotide blocks containing thiophosphoryl groups," *Nuc. Acids Res.* 21:1403–1408 (1993).
Gryaznov, et al., "Anchor for one step release of 3'–amino–oligonucleotides from a solid support," *Tetrahedron Lett.* 34:1261–1264 (1993).
Horn, et al., "Forks and combs and DNA: the synthesis of branched oligodeoxyribonucleotides," *Nuc. Acids Res.* 17: 6959–6967 (1989).
Jager, et al., "Oligonucleotide 4–alkylphosphoramidates: synthesis and binding to polynucleotides," *Biochem.* 27:7237–7246 (1988).

(List continued on next page.)

*Primary Examiner*—Eggerton A. Campbell
*Attorney, Agent, or Firm*—Stephen C. Macevicz; Vincent M. Powers

[57] ABSTRACT

Compounds referred to herein as oligonucleotide clamps are provided that stably bind to target polynucleotides in a sequence-specific manner. The oligonucleotide clamps comprise one or more oligonucleotide moieties capable of specifically binding to a target polynucleotide and one or more pairs of binding moieties covalently linked to the oligonucleotide moieties. In accordance with the invention, upon annealing of the oligonucleotide moieties to the target polynucleotide, the binding moieties of a pair are brought into juxtaposition so that they form a stable covalent or non-covalent linkage or complex. The interaction of the binding moieties of the one or more pairs effectively clamps the specifically annealed oligonucleotide moieties to the target polynucleotide.

24 Claims, 2 Drawing Sheets

OTHER PUBLICATIONS

Jaschke, et al., "Automated incorporation of polyethylene glycol into synthetic oligonucleotides," *Tetrahedron Lett.* 34:301–304 (1993).

Kabanov, et al., "A new class of antivirals: antisense oligonucleotides combined with a hydrophobic substituent effectively inhibits influenza virus reproduction and synthesis of virus–specific proteins in MDCK cells," *FEBS Lett.* 259:327–330 (1990).

Knorre, et al., "Novel antisense derivatives: antisense DNA intercalators, cleavers, and alkylators," in *Prospects for Antisense Nucleic Acid Therapy of Cancer and AIDS* (Wiley–Liss, New York, NY) pp. 195–218 (1991).

Letsinger, et al., "Synthesis and properties of modified oligonucleotides," *Nuc. Acids Res.* 24:75–78 (1991).

Letsinger, et al., "Cholesteryl–conjugated oligonucleotides: synthesis, properties, and activity as inhibitors of replication of human immunodeficiency virus in cell culture," *Proc. Natl. Acad. Sci.* 86:6553–6556 (1989).

Luebke, et al., "Nonenzymatic ligation of double–helical DNA by alternate–strand triple helix formation," *Nuc. Acids Res.* 20:3005–3009 (1992).

Ma, et al., "Design and synthesis of RNA miniduplexes via a synthetic linker approach," *Biochem.* 32:1751–1758 (1993).

MacKeller, et al., "Synthesis and physical properties of anti–HIV antisense oligonucleotides bearing terminal lipophilic groups," *Nuc. Acids Res.* 20:3411–3417 (1992).

Marabelli, et al., "In vitro and in vivo Pharmacologic Activities of Antisense Oligonucleotides" *Anti–Cancer Drug Des.* 6:647–661 (1991).

Mitsuya, H., et al., "Long–Term Inhibition of Human T–Lympho–tropic Virus Type III/Lymphadenopathy–Associated Virus (Human Immunodeficiency Virus) DNA Synthesis and RNA Expression in T Cells Protected by 2',3'–Dideoxynucleosides in Vitro" *Proc. Natl. Acad. Sci. USA* 84:2033–2037 (1987).

Mitsuya, H., et al., "3'–Azido–3'–Deoxythymidine (BW A509U): An Antiviral Agent that Inhibits the Infectivity and Cytopathic Effect of Human T–Lymphotropic Virus Type III/Lymphadenopathy–Associated Virus in Vitro" *Proc. Natl. Acad. Sci. USA* 82:7096–7100 (1985).

Mitsuya, H., and Broder, S., "Inhibition of the in Vitro Infectivity and Cytopathic Effect of Human T–Lymphotrophic Virus Type III/Lymphadenopathy–Associated Virus (HTLV–III/LAV) by 2',3'–Dideoxynucleosides" *Proc. Natl. Acad. Sci. USA* 83:1911–1915 (1986).

Mitsuya, H., and Yarchoan, R., "Development of Antiretroviral Therapy for AIDS and Related Disorders" in *Textbook of AIDS Medicine* (Broder, S., et al., Eds.) Williams & Wilkins, Baltimore, MD, pp. 721–742, Section V., Chapter 47 (1994).

Moser, et al., "Sequence–Specific Cleavage of Double Helical DNA by Triple Helix Formation," *Science* 238:645–650 (1987).

Newton, et al., "The production of PCR products with 5' single–stranded tails using primers that incorporated novel phosphoramidite intermediates," *Nuc. Acids Res.* 21:1155–1162 (1993).

Prakash, et al., "Structural effects in the recognition of DNA by circular oligonucleotides" *J. Am. Chem. Soc.* 114:3523–3527 (1992).

Reed, et al., "Acridine–and cholesterol–derivatized solid supports for improved synthesis of 14–modified oligonucleotides," *Bioconjugate Chem.* 2:217–225 (1991).

Roberts, et al., "Specificity and stringency in DNA triplex formation," *Proc. Natl. Acad. Sci.* 88:9397–9401 (1991).

Rothenberg, M., et al., "Oligonucleotides as Anti–Sense Inhibitors of Gene Expression: Therapeutic Implications," *J. Natl. Cancer Inst.* 81:1539–1544 (1989).

Rumney, et al., "DNA Recognition by Hybrid Oligoether–Oligodeoxynucleotide Macrocycles," *Angew. Chem. Int. Ed. Eng.* 31:1617–1619 (1992).

Shabarova, et al., "Chemical ligation of DNA: the first non–enzymatic assembly of a biologically active gene," *Nuc. Acids Res.* 19:4247–4251 (1991).

Shea, et al., "Synthesis, hybridization properties and antiviral activity of lipid–oligonucleotide conjugates," *Nuc. Acids Res.* 18:3777–3783 (1990).

Simons, et al., "Antisense c–myb Oligonucleotides Inhibit Intimal Arterial Smooth Muscle Cell Accumulation in Vivo," *Nature* 359:67–70 (1992).

Sokolova, et al., "Chemical reactions within DNA duplexes: cyanogen bromide as an effective oligodeoxynucleotide coupling agent," *FEBS Lett.* 232:153–155 (1988).

Stein, et al., "Mode of action of 5'–linked cholesteryl phosphorothioate oligonucleotides in inhibiting syncytia formation and infection by HIV–1 and HIV–2 in vitro," *Biochem.* 30:2439–2444 (1991).

Thuong, et al., "Oligonucleotides attached to intercalators, photoreactive and cleavage agents," in *Oligonucleotides and Analogues: A Practical Approach* (Eckstein, Ed.; IRL Press, Oxford, U.K.) (1991).

Thuong, et al., "Synthesis et reactivite d'oligothymidylates substitues par un agent intercalant et un groupe thiophosphate," *Tetrahedron Lett.* 28:4157–4160 (1987).

Uhlmann, et al., "Antisense oligonucleotides: a new therapeutic principle," *Chem. Rev.* 90:543–584 (1990).

Webster's Dictionary (Prentice Hall Press, New York, NY) p. 660 (1983).

Will, et al., "Attachment of vitamin E derivatives to oligonucleotides during solid–phase synthesis," *Tetrahedron Lett.* 33:2729–2732 (1992).

Yarchoan, R., et al., "Administration of 3'–Azido–3'–Deoxythymidine, an Inhibitor of HTLV–III/LAV Replication, to Patients with AIDS or AIDS–Related Complex," *Lancet* 8481:575–580 (1986).

Zuber, et al., "Enhanced ligation of DNA with a synthetic effector molecule," *J. Am. Chem. Soc.* 115:4939–4940 (1993).

OLIGONUCLEOTIDE CLAMPS

This application is a division of U.S. application Ser. No. 08/087,387 filed Jul. 2, 1993, U.S. Pat. No. 5,473,060.

The invention relates generally to oligonucleotides and their use as probes and therapeutic agents, and more particularly, to modified oligonucleotides whose ends are capable of spontaneously forming a stable ring structure whenever such oligonucleotide specifically binds to a target polynucleotide.

BACKGROUND

The unpredictability and expense of conventional drug discovery has led to the exploration of several drug discovery approaches that promise more systematic and/or rapid identification candidate compounds for testing in biological assays and disease models. Examples of such approaches include selection of small peptides from a synthetic or recombinant peptide libraries, e.g. Pirrung et al, U.S. Pat. No. 5,143,854; Geysen et al, J. Immunol. Meth., 102: 259–274 (1987); Lam et al, Nature, 354: 82–84 (1991); Scott et al, Science, 249: 386–390 (1990); the construction and selection of human or humanized antibodies from recombinant antibody libraries, e.g. Riechmann et al, Nature, 332: 323–327 (1988); Winter and Milstein, Nature, 349: 293–299 (1991); selection of aptamers or ribozymes from random sequence polynucleotide libraries, e.g. Ellington and Szostak, Nature, 346: 818–822 (1990); Blackwell et al, Science, 250: 1104–1110 (1990); Tuerk et al, Science, 249: 505–510 (1990); Joyce, Gene, 82: 83–87 (1989); Cech et at U.S. Pat. No. 4,987,071; Haseloff et al, Nature, 334: 585–591 (1988); and the use of antisense oligonucleotides, e.g. Uhlmann and Peyman, Chemical Reviews, 90: 543–584 (1990); Goodchild, Bioconjugate Chemistry, 1: 165–187 (1990); Helene et al, Biochim. Biophys. Acta, 1049: 99–125 (1990); Cohen, Ed., Oligonucleotides: Antisense Inhibitors of Gene Expression (Macmillan Press, New York, 1989); Crooke, Ann. Rev. Pharmacol. Toxicol., 32: 329–376 (1992); McManaway et al, Lancet, Vol. 335, pgs. 808–811 (1990); Bayever et al, Antisense Research and Development, 2: 109–110 (1992); Manson et al, Lymphokine Research, Vol. 9, pgs. 35–42 (1990); Lisziewicz et al, Proc. Natl. Acad. Sci., 90: 3860–3864 (1993); Miller, Biotechnology, Vol. 9, pgs. 358–362 (1991); Chiang et al, J. Biol. Chem., Vol. 266, pgs. 18162–18171 (1991); Calabretta, Cancer Research, Vol. 51, pgs. 4505–4510 (1991); and the like.

Of the cited examples, the antisense approach presents a compelling advantage of not requiring one or more initial screening steps to identify candidate compounds capable of binding to a predetermined target. Specific binding is achieved by providing an oligonucleotide or an analog thereof capable of forming a stable duplex or triplex with a target nucleotide sequence based on Watson-Crick or Hoogsteen binding, respectively. Thus, as soon as the sequence of a target polynucleotide is determined, the structure of candidate antisense compounds is also determined. The specifically bound antisense compound then either renders the respective targets more susceptible to enzymatic degradation, blocks translation or processing, or otherwise blocks or inhibits the function of a target polynucleotide.

Another advantage of the antisense approach has been the development of reliable and convenient methods for solid phase synthesis of polynucleotides and analogs thereof, e.g. Caruthers, Science, Vol. 230, pgs 281–285 (1985); Beaucage et al, Tetrahedron, 48: 2223–2311 (1992); and Eckstein, ed., Oligonucleotides and Analogues: A Practical Approach (IRL Press, Oxford, 1991). In particular, the availability of synthetic oligonucleotides and a variety of nuclease-resistant analogs, e.g. phosphorothioates, methylphosphonates, and the like, has encouraged investigation of antisense compounds for treating a variety of conditions associated with the inappropriate expression of indigenous and/or exogenous genes, such as described in the references cited above.

Notwithstanding the many hurdles that have been overcome in the course of developing antisense compounds, several significant uncertainties still stand in the way of their widespread adoption as drugs. One such uncertainty concerns the degree of specificity of antisense oligonucleotides under physiological conditions. Antisense oligonucleotides could be non-specific in at least two senses: (i) duplex or triplex formation may lack specificity, e.g. non-perfectly matched duplexes may form—leading to the unwanted inhibition of non-target polynucleotides, and (ii) the moieties not directly involved in base pairing, e.g. the backbone or other appendant groups, may interact non-specifically with other cellular components leading to undesired side effects, e.g. Woolf et al, Proc. Natl. Acad. Sci., 89: 7305–7309 (1992); Matsukura et al, Proc. Natl. Acad. Sci., 84: 7706–7710 (1987); and the like. In regard to first type of nonspecificity, it has been observed that duplexes involving longer oligonucleotides tend to be more tolerant of mismatches—and hence, less specific—than duplexes involving shorter oligonucleotides, e.g. Young et al, Nucleic Acids Research, 19: 2463–2470 (1991). In regard to the second type of nonspecificity, such activity may not be surprising in view of the large body of work on the use of polyanions, in particular homopolymeric polynucleotides, as anti-viral compounds, e.g. Levy, Chapter 7, in Stringfellow, editor, Interferon and Interferon Inducers (Parcel Dekker, New York, 1980). Interestingly, increased activity—and with some polyanions increased toxicity—was observed with increased polymer size.

The uncertainty over nonspecific binding has led to the exploration of several ways to modify oligonucleotides to enhance duplex or triplex stability of antisense compounds. One approach has been to couple duplex or triplex intercalating moieties to the antisense oligonucleotide, e.g. Park et al, Proc. Natl. Acad. Sci., 89: 6653–6657 (1992); Stein et al, Gene, 72: 333–341 (1988); Mergny et al, Science, 256: 1681–1684 (1992); Miller, International application PCT/US92/03999; and the like. Another approach involves the use of circular oligonucleotides, which are exonuclease resistant and have been shown to melt from single-stranded targets at substantially higher temperatures than linear oligonucleotides when binding involves both Watson-Crick and Hoogsteen base pairing, e.g. Prakash and Kool, J. Am. Chem. Soc., 114: 3523–3527 (1992).

Additional approaches for enhancing specificity and binding strength would be highly useful for DNA-based therapeutics and diagnostic applications of nucleic acids.

SUMMARY OF THE INVENTION

The invention relates to compounds capable of forming stable circular complexes and/or covalently closed macrocycles after specifically binding to a target polynucleotide. Generally, compounds of the invention comprise one or more oligonucleotide moieties capable of specifically binding to a target polynucleotide and one or more pairs of binding moieties covalently linked to the oligonucleotide moieties. In accordance with the invention, upon annealing of the oligonucleotide moieties to the target polynucleotide, the binding moieties of a pair are brought into juxtaposition so that they form a stable covalent or non-covalent linkage or complex. The interaction of the binding moieties of the one or more pairs effectively clamps the specifically annealed oligonucleotide moieties to the target polynucleotide.

Figure 1A:
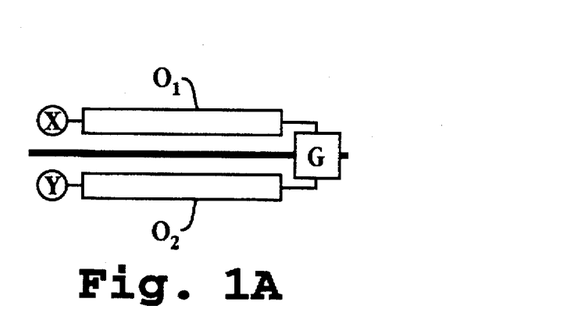
FIGS. 1a–c diagrammatically illustrate how three separate embodiments of the invention bind or "clamp" a target polynucleotide.

In one aspect, compounds of the invention comprise a first binding moiety, a first oligonucleotide moiety, a hinge region, a second oligonucleotide moiety, and a second binding moiety, for example, as represented by the particular embodiment of the following formula:

wherein $O_1$ and $O_2$ are the first and second oligonucleotide moieties, G is the hinge region, X is the first binding moiety and Y is the second binding moiety such that X and Y form a stable covalent or non-covalent linkage or complex whenever they are brought into juxtapositon by the annealing of the oligonucleotide moieties to a target polynucleotide, as illustrated diagrammatically in FIG. 1a. Preferably, in this embodiment, one of $O_1$ and $O_2$ forms a duplex through Watson-Crick type of binding with the target polynucleotide while the other of $O_1$ and $O_2$ forms a triplex through Hoogsteen or reverse Hoogsteen type of binding. Whenever X and Y form a covalent linkage, the compound of the invention forms a macrocycle of the following form:

wherein "XY" is the covalent linkage formed by the reaction of X and Y.

Figure 1B:
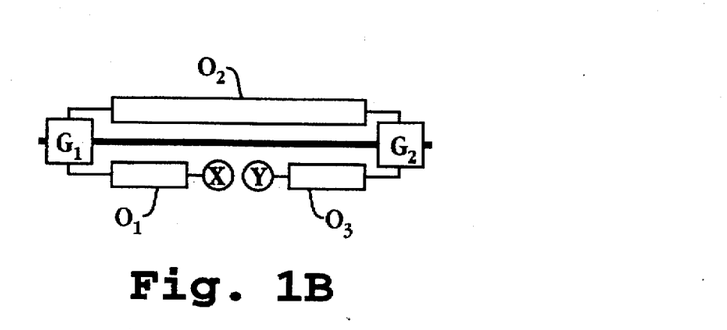

In another aspect, compounds of the invention comprise a first binding moiety, a first, second, and third oligonucleotide moiety, a first and second hinge region, and a second binding moiety, for example, as represented by the particular embodiment of the following formula:

wherein X and Y are described as above, $G_1$ and $G_2$ are the first and second hinge regions, and $O_1$, $O_2$, and $O_3$ are the first through third oligonucleotide moieties. Preferably, the sequences of $O_1$, $O_2$, and $O_3$ are selected so that $O_1$ and $O_2$ and $O_3$ and $O_2$ form triplex structures with the target polynucleotide, as diagrammatically illustrated in FIG. 1b. Whenever X and Y form a covalent linkage, the compound of the invention forms a macrocycle of the following form:

wherein "XY" is the covalent linkage formed by the reaction of X and Y.

Figure 1C:
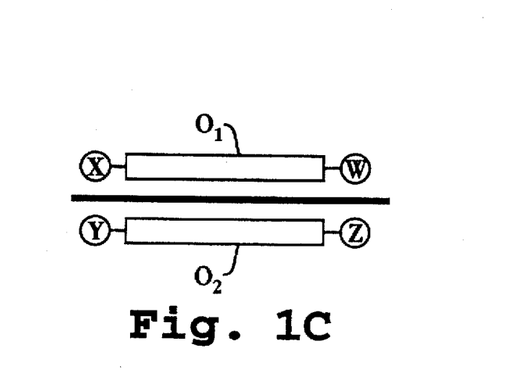

In yet another aspect, the oligonucleotide clamps of the invention are compositions of two or more components, e.g. having the form:

and wherein X, Y, W, and Z are defined as X and Y above. In this embodiment, the hinge region is replaced by additional complex-forming moieties W and Z. As above, one of $O_1$ and $O_2$ undergoes Watson-Crick type of binding while the other undergoes Hoogsteen or reverse Hoogsteen type of binding to a target polynucleotide, as shown diagrammatically in FIG. 1c. Similarly, whenever X and Y and W and Z form covalent linkages, compounds X—$O_1$—W and Y—$O_2$—Z form a macrocycle of the following form:

depending on the selection of $O_1$ and $O_2$.

Preferably, compounds of the invention are capable of forming covalently closed macrocycles or stable circular complexes topologically linked to a target polynucleotide.

The invention provides compounds capable of specifically binding to predetermined target polynucleotides with superior stability than currently available probes and antisense compounds. Compounds of the invention are employed either as antisense or anti-gene compounds to inhibit the function of a polynucleotide whose expression or participation in a regulatory function is associated with a disease state or as probes for detecting the presence of a target polynucleotide. The invention includes the oligonucleotide clamps per se as well as pharmaceutical compositions and kits for particular applications.

Definitions

As used herein, the symbols $O_1$, $O_2$, and $O_3$ refer to oligonucleotides or oligonucleotide segments having the binding attributes defined in the Summary of the Invention section above. If desired, the symbols $O_1$, $O_2$, and $O_3$ as used herein may also be referred to as oligo1, oligo2, and oligo3, respectively.

Figure 2A:
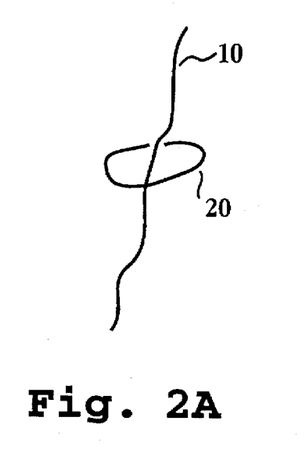
FIGS. 2a–b diagrammatically illustrates the concept of "topologically linked."
Figure 2B:
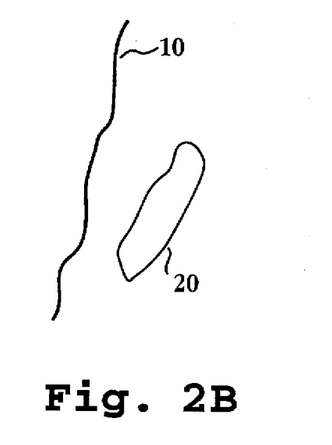

"Topologically linked" in reference to compounds of the invention refers to the relative configuration of target polynucleotide and oligonucleotide clamp wherein the oligonucleotide clamp forms a closed circular complex or macrocycle enclosing the target polynucleotide strand, as shown diagrammatically in FIGS. 2a and 2b. In FIG. 2a, oligonucleotide clamp 20 is topologically linked to target polynucleotide 10. In FIG. 2b, oligonucleotide 20 is topologically disjoint from target polynucleotide 10.

"Stable" in reference to the formation of a covalent linkage and/or non-covalent complex between binding moieties means that melting temperature of the oligonucleotide clamp incorporating the given pair(s) of binding moieties and its target polynucleotide is increased by at least fifty percent over the melting temperature of oligonucleotide moieties of the clamp alone, wherein melting temperature is measured by standard techniques, e.g. half maximum of 260 nm absorbance v. temperature as described more fully below.

"Linkage" in reference to the reaction of binding moieties includes both covalent linkages and non-covalent complexes.

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilinothioate, phosphoranilidate, phosphoramidate, and the like.

As used herein, "nucleoside" includes the natural nucleosides, including 2'-deoxy and 2'-hydroxyl forms, e.g. as described in Kornberg and Baker, DNA Replication, 2nd Ed. Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like.

DETAILED DESCRIPTION OF THE INVENTION

The invention relates to oligonucleotide clamps that are capable of binding to a specific region of a target polynucleotide. The clamping aspect of the compounds is achieved by the formation of stable linkages or complexes between binding moieties after they are brought into proximity by specific binding of the one or more oligonucleotide moieties to a target polynucleotide. Preferably, oligonucleotide moieties of the compounds of the invention are selected so that they simultaneously undergo Watson-Crick and Hoogsteen types of binding with specific regions of a target polynucleotide.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267:5712–5721 (1992); Yoon et al, Proc. Natl. Acad. Sci., 89: 3840–3844 (1992); Blume et al, Nucleic Acids Research, 20: 1777–1784 (1992); and the like. Generally, after one of the oligonucleotide moieties forms a Watson-Crick duplex with a pryimidine-rich or purine-rich track in a target polynucleotide, the remaining oligonucleotide components bind to the major groove of the duplex to form a triplex structure.

Selection of particular oligonucleotide sequences for triplex formation can also be carried out empirically, for example, through aptamer screening, or like process, where candidate oligonucleotide moieties are selected on the basis of binding strength to an immobilized double stranded target, e.g. Ellington and Szostak, Nature, 346: 818–822 (1990); Toole et al, International application PCT/US92/01383; and the like.

Target polynucleotides may be single stranded or double stranded DNA or RNA; however, single stranded DNA or RNA target polynucleotides are preferred.

Preferably, stability of oligonucleotide clamp/target polynucleotide complexes are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and clamp concentrations at between about 1.0–2.0 μM. Typical conditions are as follows: 150 mM NaCl and 10 mM $MgCl_2$ in a 10 mM sodium phosphate buffer (pH 7.0) or in a 10 mM Tris-HCl buffer (pH 7.0); or like conditions. Data for melting curves are accumulated by heating a sample of the oligonucleotide clamp/target polynucleotide complex from room temperature to about 85°–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UV/VIS spectrophotometer and model HP 89100A temperature controller, or like instruments.

The oligonucleotide moieties of the invention are synthesized by conventional means on a commercially available automated DNA synthesizer, e.g. an Applied Biosystems (Foster City, Calif.) model 380B, 392 or 394 DNA/RNA synthesizer. Preferably, phosphoramidite chemistry is employed, e.g. as disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. For therapeutic use, nuclease resistant backbones are preferred. Many types of modified oligonucleotides are available that confer nuclease resistance, e.g. phosphorothioate, phosphorodithioate, phosphoramidate, or the like, described in many references, e.g. phosphorothioates: Stec et al, U.S. Pat. No. 5,151,510; Hirschbein, U.S. Pat. No. 5,166,387; Bergot, U.S. Pat. No. 5,183,885; phosphoramidates: Froehler et al, International application PCT/US90/03138; and for a review of additional applicable chemistries: Uhlmann and Peyman (cited above). In some embodiments it may be desirable to employ P-chiral linkages, in which case the chemistry disclosed by Stec et al European patent application 92301950.9, may be appropriate.

The length of the oligonucleotide moieties is sufficiently large to ensure that specific binding will take place only at the desired target polynucleotide and not at other fortuitous sites. The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, and the like. Preferably, the oligonucleotide moieties have lengths in the range of about 6 to 40 nucleotides. More preferably, the oligonucleotide moieties have lengths in the range of about 12 to 25 nucleotides.

Hinge regions consist of nucleosidic or non-nucleosidic polymers which preferably facilitate the specific binding of the monomers of the oligonucleotide moieties with their complementary nucleotides of the target polynucleotide. Generally, the oligonucleotide moieties may be connected to hinge regions and/or binding moieties in either 5'→3' or 3'→5' orientations. For example, in the embodiment described above comprising a first binding moiety, a first oligonucleotide moiety, a hinge region, a second oligonucleotide moiety, and a second binding moiety, the oligonucleotide moieties may have any of the following orientations:

OR

OR

OR wherein $N_1N_2N_3$—...—$N_k$ and $N_1N_2N_3$—...—$N_j$ are k-mer and j-mer oligonucleotide moieties in the indicated orientations.

Preferably, the hinge region has the general form:

wherein M may be an inert non-sterically hindering spacer moiety serving to connect the oligonucleotide moieties, wherein the M's and L's in any given chain may be the same or different. Alternatively, one or more of monomers M may contain reactive functionalities for attaching labels; oligonucleotides or other binding polymers for hybridizing or binding to amplifier strands or structures, e.g. as described by Urdea et al, U.S. Pat. No. 5,124,246 or Wang et al, U.S. Pat. No. 4,925,785; "hooks", e.g. as described in Whiteley et al, U.S. Pat. No. 4,883,750; or other groups for affecting solubility, cellular delivery, promotion of duplex and/or triplex formation, such as intercalators, alkylating agents, and the like. Preferably, the hinge regions provide a spacer of about 16–28 angstroms between the termini of the oligonucleotides.

Preferably, L is a phosphorus(V) linking group which may be phosphodiester, phosphotriester, methyl or ethyl phosphonate, phosphorothioate, phosphorodithioate, phosphoramidate, or the like. Generally, linkages derived from phosphoramidite precursors are preferred so that compounds of the invention can be conveniently synthesized with commercial automated DNA synthesizers, e.g. Applied Biosystems, Inc. (Foster City, Calif.) model 394, or the like.

n may vary significantly depending on the nature of M and L. Generally, n will vary from 1 for M comprising alkyl, alkenyl, and/or ethers containing 10 or more carbon atoms, e.g. Salunkhe et al, J. Am. Chem. Soc., 114: 8768–8772 (1992), to about 10 for M comprising alkyl, alkenyl, and/or ethers containing 2–3 carbon atoms. Preferably, for a hinge moiety consisting entirely of an alkyl chain (and linkage moieties), such alkyl chain contains form 8 to 15 carbon atoms, and more preferably, from 9 to 12 carbon atoms. Preferably, for nucleoside-sized monomers, n varies between about 3 and about 10; and more preferably, n varies between about 4 and 8.

Preferably, hinge moieties are synthesized using conventional phosphoramidite and/or hydrogen phosphonate chemistries. The following references disclose several phosphoramidite and/or hydrogen phosphonate monomers suitable for use in the present invention and provide guidance for their synthesis and inclusion into oligonucleotides: Newton et al, Nucleic Acids Research, 21: 1155–1162 (1993); Griffin et al, J. Am. Chem. Soc., 114: 7976–7982 (1992); Jaschke et al, Tetrahedron Letters, 34: 301–304 (1992); Ma et al, International application PCT/CA92/00423; Zon et al, International application PCT/US90/06630; Durand et al, Nucleic Acids Research, 18: 6353–6359 (1990); Salunkhe et al, J. Am. Chem. Soc., 114: 8768–8772 (1992); and the like.

In a preferred embodiment, M is a straight chain, cyclic, or branched organic molecular structure containing from 1 to 20 carbon atoms and from 0 to 10 heteroatoms selected from the group consisting of oxygen, nitrogen, and sulfur. More preferably, M is alkyl, alkoxy, alkenyl, or aryl containing from 1 to 16 carbon atoms; heterocyclic having from 3 to 8 carbon atoms and from 1 to 3 heteroatoms selected from the group consisting of oxygen, nitrogen, and sulfur, glycosyl; or nucleosidyl. Most preferably, M is alkyl, alkoxy, alkenyl, or aryl containing from 1 to 8 carbon atoms; glycosyl; or nucleosidyl.

A variety of binding moieties are suitable for use with the invention. Generally, they are employed in pairs, which for convenience here will be referred to as X and Y. X and Y may be the same or different. Whenever the interaction of X and Y is based on the formation of stable hydrophobic complex, X and Y are lipophilic groups, including alkyl groups, fatty acids, fatty alcohols, steroids, waxes, fat-soluble vitamins, and the like. Further exemplary lipophilic binding moieties include glycerides, glyceryl ethers, phospholipids, sphingolipids, terpenes, and the like. In such embodiments, X and Y are preferably selected from the group of steroids consisting of a derivatized perhydrocyclopentanophenanthrene nucleus having from 19 to 30 carbon atoms, and 0 to 6 oxygen atoms; alkyl having from 6 to 16 carbon atoms; vitamin E; and glyceride having 20 to 40 carbon atoms. Preferably, a perhydrocyclopentanophenanthrene-based moiety is attached through the hydroxyl group, either as an ether or an ester, at its C3 position. It is understood tha X and Y may include a linkage group connecting it to an oligonucleotide moiety. For example, glyceride includes phosphoglyceride, e.g. as described by MacKellar et al, Nucleic Acids Research, 20: 3411–3417 (1992), and so on. It is especially preferred that lipophilic moieties, such as perhydrocyclopentanophenanthrene derivatives, be linked to the 5' carbon and/or the 3' carbon of an oligonucleotide moiety by a short but flexible linker that permits the lipophilic moiety to interact with the bases of the oligonucleotide clamp/target polynucleotide complex or a lipophilic moiety on the same or another oligonucleotide moiety. Such linkers include phosphate (i.e. phosphodiester), phosphoramidate, hydroxyurethane, carboxyaminoalkyl and carboxyaminoalkylphosphate linkers, or the like. Preferably, such linkers have no more than from 2 to 8 carbon atoms.

Binding moieties can be attached to the oligonucleotide moiety by a number of available chemistries. Generally, it is preferred that the oligonucleotide be initially derivatized at its 3' and/or 5' terminus with a reactive functionality, such as an amino, phosphate, thiophosphate, or thiol group. After derivatization, a hydrophilic or hydrophobic moiety is coupled to the oligonucleotide via the reactive functionality. Exemplary means for attaching 3' or 5' reactive functionalities to oligonucleotides are disclosed in Fung et al, U.S. Pat. No. 5,212,304; Connolly, Nucleic Acids Research, 13: 4485–4502 (1985); Tino, International application PCT/US91/09657; Nelson et al, Nucleic Acids Research, 17: 7187–7194 (1989); Stabinsky, U.S. Pat. No. 4,739,044; Gupta et al, Nucleic Acids Research, 19: 3019 (1991); Reed et al, International application PCT/US91/06143; Zuckerman et al, Nucleic Acids Research, 15: 5305 (1987); Eckstein, editor, Oligonucleotides and Analogues: A Practical Approach (IRL Press, Oxford, 1991); Clontech 1992/1993 Catalog (Clontech Laboratories, Palo Alto, Calif.); and like references.

Preferably, whenever X and Y form a covalent linkage, X and Y pairs must react specifically with each other when brought in juxtaposition, but otherwise they must be substantially unreactive with chemical groups present in a cellular environment. In this aspect of the invention, X and Y pairs are preferably selected from the following group: when one of X or Y is phosphorothioate, the other is haloacetyl, haloacyl, haloalkyl, or alkylazide; when one of X or Y is thiol, the other is alkyl iodide, haloacyl, or haloacetyl; when one of Y or Y is phenylazide the other is phenylazide. More preferably, when one of X or Y is phosphorothioate, the other is haloacetyl, haloacyl, or haloalkyl, wherein said alkyl, acetyl, or acyl moiety contains from one to eight carbon atoms.

Most preferably, when one of X or Y is phosphorothioate, the other is haloacetyl. Most preferably, whenever one of X or Y is phosphorothioate, the other is bromoacetyl. These binding moieties form a covalent thiophosphoylacetylamino bridge, as shown below, selectively and efficiently at low concentrations, e.g. less than one μM, when reacted in an aqueous environment in the presence of a target polynucleotide:

5'-N₁N₂N₃...Nⱼ-NHC(=O)CH₂X +
1

S⁻P(=O)(O⁻)O—N₁N₂N₃...Nₖ-3' ⟶
2

N₁N₂N₃...Nⱼ-NHC(=O)CH₂SP(=O)(O⁻)O—N₁N₂N₃...Nₖ wherein X is halo and N₁, N₂,... Nⱼ and Nₖ are nucleotides of a j-mer and k-mer, respectively. Compound 1 can be prepared by N-succinimidyl haloacetate in N,N-dimethylformamide (DMF) with a 3'-aminodeoxyribonucleotide precursor in a sodium borate buffer at room temperature. After about 35 minutes the mixture is diluted (e.g. with H₂O), desalted and, purified, e.g. by reverse phase HPLC. The 3'-aminodeoxyribonucleotide precursor can be prepared as described in Gryaznov and Letsinger, Nucleic Acids Research, 20: 3403–3409 (1992) or Tetrahedron Letters, 34: 1261–1264 (1993). Briefly, after deprotection, the 5' hydroxyl of a deoxythymidine linked to a support via a standard succinyl linkage is phosphitylated by reaction with chloro-(diisopropylethylamino)-methoxyphosphine in an appropriate solvent, such as dichloromethane/diisopropylethylamine. After activation with tetrazole, the 5'-phosphitylated thymidine is reacted with a 5'-trityl-O-3'-amino-3'-deoxynucleoside to form a nucleoside-thymidine dimer wherein the nucleoside moieties are covalently joined by a phosphoramidate linkage. The remainder of the oligonucleotide is synthesized by standard phosphoramidite chemistry. After cleaving the succinyl linkage, the oligonucleotide with a 3' terminal amino group is generated by cleaving the phosphoramidate link by acid treatment, e.g. 80% aqueous acetic acid for 18–20 hours at room temperature. 5'-trityl-O-3'-amino-3'-deoxynucleosides may be synthesized in accordance with Glinski et al, J. Chem. Soc. Chem. Comm., 915–916 (1970); Miller et al, J. Org. Chem. 29: 1772 (1964); Zielinki and Orgel, Nucleic Acids Research, 13: 2469–2484 (1985) and 15: 1699–1715 (1987); Ozols et al, Synthesis, 7: 557–559 (1980); and Azhayev et al, Nucleic Acids Research, 6: 625–643 (1979); which references are incorporated by reference.

5' monophosphorothioate 2 is formed as follows: A 5' monophosphate is attached to the 5' end of an oligonucleotide either chemically or enzymatically with a kinase, e.g. Sambrook et al, Molecular Cloning: A Laboratory Manual, 2nd Edition (Cold Spring Harbor Laboratory, New York, 1989). Preferably, as a final step in oligonucleotide synthesis, a monophosphate is added by chemical phosphorylation as described by Horn and Urdea, Tetrahedron Lett., 27: 4705 (1986) (e.g. using commercially available reagents such as 5' Phosphate-ON™ from Clontech Laboratories Palo Alto, Calif.)). The 5'-monophosphate is then sulfurized using conventional sulfurizing agents, e.g. treatment with a 5% solution of S₈ in pyridine/CS₂ (1:1, v/v, 45 minutes at room temperature); or treatment with sulfurizing agent described in U.S. Pat. Nos. 5,003,097; 5,151,510; or 5,166,387. Preferably, the haloacetylamino derivatized oligonucleotides are synthesized separately from unprotected monophosphorothioate groups.

Compounds of the invention can be employed as diagnostic probes to detect the presence of one or more target polynucleotides in a wide range of samples, including environmental samples, e.g. from public water supplies, samples from foodstuffs, and from other biological samples, such as blood, saliva, semen, amniotic fluid, tissue homogenates of plants or animals, or of human patients, and the like. The use of nucleic acid probes in human diagnostics, forensics, and genetic analysis has been extensively reviewed. For example, the following references describe many diagnostic applications of nucleic acid probes for which the present invention can be usefully employed: Caskey, Science 236: 1223–1228 (1987); Landegren et al, Science, 242: 229–237 (1988); and Arnheim et al, Ann. Rev. Biochem., 61: 131–156 (1992). Moreover, there is extensive guidance in the literature concerning the selection of hybridization conditions, labeling means, and the like, which is applicable to the practice of the present invention, e.g. Wallace et al, Nucleic Acids Research 6: 3543–3557 (1979); Crothers et al, J. Mol. Biol. 9: 1–9 (1964); Gotoh, Adv. Biophys. 16: 1–52 (1983); Wetmer, Critical Reviews in Biochemistry and Molecular Biology 26: 227–259 (1991); Breslauer et al, Proc. Natl. Acad. Sci. 83: 3746–3750 (1986); Wolf et al, Nucleic Acids Research, 15: 2911–2926 (1987); McGraw et al, Biotechniques, 8: 674–678 (1990), and the like.

Oligonucleotide clamps of the invention may be used in essentially any of the known solution or solid phase hybridization formats, such as those in which the analyte is bound directly to a solid phase, or sandwich hybridizations in which the analyte is bound to an oligonucleotide that is, in turn, bound to a solid phase. Oligonucleotide clamps having an oligonucleotide "tail" attached to a hinge region are particularly useful in conjunction with branched polymer amplification schemes, such as those disclosed by Urdea et al, U.S. Pat. No. 5,124,246; Wang et al, U.S. Pat. No. 4,925,785; and the like. Urdea et al and Wang et al are incorporated by reference for their description of such hybridization assays. In such embodiments, the oligonucleotide clamp serves as a highly stable "capture" probe by binding to a target polynucleotide analyte of interest. The oligonucleotide tail then hybridizes with a directly or indirectly labeled amplifier strand or complex. Such tails are long enough to form a stable duplex with the amplifier strand. Preferably, such tails are between 18 and 60 nucleotides in length. Tails may also comprise a second oligonucleotide clamp. That is, a dimer of oligonucleotide clamps having different binding specificities can be used to tightly couple an amplifier complex to a target polynucleotide.

Preferably, oligonucleotide tails are coupled to hinge regions at an amino group which has been derivatized with bromoacetyl. An oligonucleotide tail having either a 5' or 3' phosphorothioate group is then reacted with the bromoacetyl group to form a thiophosphorylacetylamino bridge, as described more fully above and in the Examples below. Phosphoramidate linkages are introduced in accordance with published procedures, e.g. Letsinger, U.S. Pat. No. 4,958,013; Agrawal et al, Nucleic Acids Research, 18: 5419–5423 (1990); or the like. By a similar procedure, dimers of oligonucleotide clamps can also be constructed.

Whenever oligonucleotide clamps of the invention are employed in diagnostic assays, or in other processes not requiring direct contact with a patient, a wider range of binding moieties may be employed than would be possible for therapeutic use. In diagnostic and other non-therapeutic applications, reaction of the binding moieties may involve an activation step wherein one or both of the binding moieties are activated or rendered reactive towards one another by exposure to an activating agent or condensing agent, such as radiation, a reducing agent, an oxidizing agent, or the like. Exemplary, binding moieties employing activating agents include thiophosphoryl groups in the presence of $K_3Fe(CN)_6$ or $KI_3$, e.g. Gryaznov and Letsinger, Nucleic Acids Research, 21: 1403–1408 (1993); phosphoryl and hydroxyl in the presence of N-cyanoimidazole, e.g. Luebke et al, J. Am. Chem. Soc., 113: 7447–7448 (1991); phosphoryl or amino group and hydroxyl in the presence of cyanogen bromide, e.g. Sokolova et al, FEBS Letters, 232: 153–155 (1988); phosphoryl and hydroxyl groups in the presence of spermine-5-(N-ethylimidazole)carboxamide and cyanoimidazole, e.g. Zuber et.al., J. Am. Chem. Soc., 115: 4939–4940 (1993); and the like.

Kits incorporating oligonucleotide clamps can take a variety of forms depending on the particular embodiment, the type of assay format employed, and the labeling scheme employed. Generally, kits of the invention comprise an oligonucleotide clamp specific for a given target polynucleotide, a hybridization buffer, and a signal generation moiety. Kits of the invention may further comprise wash buffers for removing unbound label and/or oligonucleotide clamps, solid phase supports such as derivatized magnetic beads, or the like; and prehybridization buffers containing blocking agents, e.g. Denhardt's solution, sonicated salmon sperm DNA, detergents such as 1% SDS, or the like, for minimizing nonspecific binding of oligonucleotide clamps or other nucleosidic binding components, such as amplifier strands. An exemplary hybridization buffer comprises the following reagents: 100–150 mM NaCl, 10 mM $MgCl_2$, and 10 mM Tris-HCl (pH 7.0).

Signal generation moieties are molecular structures that directly or indirectly generate a signal, e.g. fluorescent, colorimetric, radioactive, or the like, that can be detected by conventional means. Direct signal generation means that the moiety producing a signal is covalently linked to the oligonucleotide clamp, e.g. as with the covalent attachment of a fluorescent dye, enzyme, or the like. Indirect signal generation means that a particular moiety, e.g. an oligonucleotide tail on a hinge region, is one component of a multicomponent system that produces a signal. Preferably, the signal generation moieties comprises an oligonucleotide tail of about 12 to about 50 nucleotides in length covalently attached to a hinge region of an oligonucleotide clamp. In one aspect of this preferred embodiment, a signal is generated indirectly by providing a second oligonucleotide which is complementary to the tail and which has a fluorescent dye covalently attached. Attaching fluorescent dyes to oligonucleotides is well known in the art, e.g. U.S. Pat. Nos. 4,997,828; 5,151,507; 4,855,225; 5,188,934; Eckstein, editor (cited above); and the like.

Compounds of the invention can be employed as components of pharmaceutical compositions. A variety of diseases and disorders can be treated by administration of a composition comprising compounds of the invention. Viral diseases that can be treated by antisense inhibition of nucleic acid expression include, but are not limited to, those caused by hepatitis B virus, cytomegalovirus, herpes simplex virus I or II, human immunodeficiency virus type I or II, influenza virus, respiratory syncytial virus, and human papilloma virus. Malignancies which can be treated by administration of antisense compounds of the invention include those known to be directly or indirectly caused by the inappropriate expression of one or more gene, such as cancers caused by the inappropriate expression of oncogenes, e.g. myb, bcr-abl, kit, myc, ras, raf, abl, or the like. In such diseases, the compounds of the invention are specifically targeted to aberrantly expressed genes associated with the diseases, or to regulatory polynucleotides that interact with aberrantly transcribed or expressed genes, e.g. Aaronson, Science, Vol. 254, pgs. 1146–1153 (1991). Acute inflammatory and immune reactions, such as septic shock, eosinophilia, and the like, can also be treated with compounds of the invention, wherein inappropriately and/or aberrantly expressed cytokine genes are inhibited, e.g. Tracey et al, Nature, Vol. 330, pgs. 662–664 (1987), U.S. Pat. No. 5,055,447, and Waage et al, J. Exp. Med., Vol. 169, pgs. 333–338 (1989) (antisense TNF-α and/or TNF-β); Starnes et al, J. Immunol., Vol. 145, pgs. 4185–4191 (1990), and Fong et al, J. Immunol., Vol. 142, pgs. 2321–2324 (antisense IL-6); Coffman et al, Science, Vol. 245 pgs. 308–310 (antisense IL-5); Finkelman et al, J. Immunol., Vol. 141, pgs. 2335–2341 (1988) (antisense IL-4); Young et al, Blood, Vol. 68, pgs. 1178–1181 (1986) (antisense GM-CSF); and the like.

The components included in pharmaceutical compositions of the invention depend on several factors, including the nature of the disease or condition being treated, the location of disease lesions, the mode of drug delivery and/or administration contemplated, the latter of which can include in vivo administration by way of regional or systemic perfusion, topical application, intranasal administration, administration by implanted or transdermal sustained release systems, and the like, as well as ex vivo administration for use in bone marrow purging. A preferred method of administration of oligonucleotide clamps comprises either regional or systemic perfusion. According to a method of regional perfusion, the afferent and efferent vessels supplying the extremity containing a lesion, e.g. a cancerous lesion, are isolated and connected to a low-flow perfusion pump in continuity with an oxygenator and heat exchanger. The iliac vessels may be used for perfusion of the lower extremities. The axillary vessels are cannulated high in the axilla for upper extremity lesions. A pharmaceutical composition containing an oligonucleotide clamp is added to the perfusion circuit, and the perfusion is continued for an appropriate time period, e.g. an hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher dosed of chemotherapeutic agent than would otherwise be tolerated upon infusion into the arterial or venous systemic circulation.

For systemic infusion, the oligonucleotide clamps are preferably delivered via a central venous catheter, which is connected to an appropriate continuous infusion device. Indwelling catheters provide long term access to the intravenous circulation for frequent administrations of drugs over extended periods of time.

Generally a pharmaceutical composition of the invention facilitates the delivery of an effective amount of the active drug to a desired site in a manner consistent with patient safety and comfort. An effective amount of an oligonucleotide clamp depends on several factors, including the disease or condition being treated, the method of administration, the scheduling of the administration, the condition of the patient, and the like. Typically, a parentially administered dose will be in the range of about 1 µg/kg/day to about 100 mg/kg/day of patient body weight. A key factor in selecting an appropriate dose for a given condition or disease is the therapeutic result, as measure by standard criteria well known to the medical practitioner, e.g. for oncological applications see: Cancer: Principles and Practice of Oncology, 3rd Edition, edited by V. T. DeVita et al (Lippincott Company, Philadelphia, 1989).

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH and the like. For example, in water soluble formulations the pharmaceutical composition preferably includes a buffer such as a phosphate buffer, or other organic acid salt, preferably at a pH of between about 7 and 8. For formulations containing weakly soluble oligonucleotide clamps, microemulsions may be employed, for example by using a nonionic surfactant such as Tween 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

Compounds of the invention include the pharmaceutically acceptable salts thereof, including those of alkaline earths, e.g. sodium or magnesium, ammonium or $NX_4^+$, wherein X is $C_{1-4}$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

Sustained release systems suitable for use with the pharmaceutical compositions of the invention include semipermeable polymer matrices in the form of films, microcapsules, or the like, comprising polylactides, copolymers of L-glutamic acid and gamma-ethyl-L-glutamate, poly(2-hydroxyethyl methacrylate), and like materials. Sustained release systems also include liposomally entrapped oligonucleotide clamps, e.g. as described in Liposome Technology, Vol. II, Incorporation of Drugs, Proteins, an Genetic Material (CRC Press).

EXAMPLE 1

Synthesis of Oligonucleotide Clamp having 3' and 5' Cholesterol Binding Moieties for pol and nef genes of HIV A series of oligonucleotide clamps were synthesized that have cholesterol moieties attached to either a 5' end, a 3' end, or to both a 3' end and a 5' end. The 3' cholesterol was attached by first constructing a cholesterol-derivatized solid phase support followed by routine oligonucleotide chain extension via phosphoramidite monomers on a conventional automated DNA synthesizer (Applied Biosystems model 394). The 5' cholesterol was attached in the final coupling step of the synthesis by reacting cholesterol chloroformate with the terminal nucleotide having a 5' amino group or by coupling a cholesterol phosphoramidite with a terminal hydroxyl group, the former method usually giving higher yields.

(1) A polymer supported oligonucleotide, 1 µmole scale, with terminal 5'-amino group was treated with 2 ml of a 10% solution of cholesteryl formate in chloroform/diisopropylethylamine (9:1, v:v) for 20 minutes at room temperature. The polymer support was then washed with chloroform and acetonitrile, cleaved and deprotected with concentrated ammonium (5 hours at 55° C.), and purified by reverse phase HPLC.

(2) A polymer supported oligonucleotide, 1 µmole scale, with terminal hydroxyl group was treated with 250 µl of 0.1M solution of cholesterol phosphoramidite in chloroform and 250 µl of 0.45M solution of tetrazole in acetonitrile for 10–15 minutes at room temperature. The polymer support was then washed with acetonitrile, cleaved and deprotected with concentrated ammonium (5 hours at 55° C.), and purified by reverse phase HPLC.

EXAMPLE 2

ATH8 Assay of Oligonucleotide Clamps Specific for pol and nef genes of HIV

The oligonucleotides and oligonucleotide clamps listed in the Table I below were synthesized in accordance with Example 1 for specific binding to the following single stranded or double stranded target polynucleotides:

TABLE I

5'-AAAAGAAAAGGGGGGA-3'
3'-TTTTCTTTTCCCCCCT-5'
Double stranded DNA
5'-AAAAGAAAAGGGGGGA-3'
Single stranded RNA or DNA

| Designation | Sequence of Oligonucleotide Clamp* |
|---|---|
| 050A | 5'-CACTTTTC$^{Me}$TTTTCCCCCCTCACACTCCCCCCTTTTCTTTTAC-Chol |
| 050B | 5'-Chol-CACTTTTC$^{Me}$TTTTCCCCCCTCACACTCCCCCCTTTTCTTTTAC-Chol |
| 051 | 5'-Chol-CACTTTTC$^{Me}$TTTTC$^{Me}$C$^{Me}$C$^{Me}$C$^{Me}$C$^{Me}$C$^{Me}$TCACACTCCCCCCTTTTCTTTTAC-Chol |
| 052A | 5'-CACTTTTC$^{Me}$TTTTCCCCCCTCACACTC$^{Me}$C$^{Me}$C$^{Me}$C$^{Me}$C$^{Me}$C$^{Me}$TTTTCTTTTAC-Chol |
| 052B | 5'-Chol-CACTTTTC$^{Me}$TTTTCCCCCCTCACACTC$^{Me}$C$^{Me}$C$^{Me}$C$^{Me}$C$^{Me}$C$^{Me}$TTTTCTTTTAC-Chol |
| 053 | 5'-Chol-CACTTTTC$^{Me}$TTTTGGGGGGTCACACTCCCCCCTTTTCTTTTAC-Chol |
| DL015 | 5'-CACTTTTCTTTTGGGGGGTCACACTCCCCCCTTTTCTTTTAC |
| DL014 | 5'-CACTTTTCTTTTGGGGGGTCACACTCCCCCCTTTTCTTTTAC-Chol |
| DL013 | 5'-Chol-CACTTTTCTTTTGGGGGGTCACACTCCCCCCTTTTCTTTTAC-Chol |
| DL021 | 5'-Chol-TTTTCTTTTCACACTTTTCTTTTGGGGGGTCACACTCCCCCC-Chol |
| DL022 | 5'-Chol-CACTTTTCTTTTCCCCCCTCACACACTCCCCCCTTTTCTTTTAC-Chol |
| DL023 | 5'-Chol-TTTTCTTTTCACACTTTTCTTTTCCCCCCTCACTCCCCCC-Chol |

*"Chol" represents cholesterol and C$^{Me}$ represents 5-methylated cytidine.

The melting temperature of the following compounds were determined by computing the half maximum of the 260 nm absorption v. temperature curve, as described above: DL015:39.0° C.; DL014: 58° C.; DL013: 68.0° C.; DL021: 67.5° C.; DL022: 67.5° C.; and control (two unconnected oligonucleotides without binding moieties having sequences: 3'-TTTTCTTTTCCCCCCT-5' and 5'-TTTTC$^{Me}$TTTT(C$^{Me}$)$_6$-3'): 32.0° C.

Each of the compounds of Table I were tested in an ATH8 cell assay to assess the inhibition of the cytopathic effects of HIV infection on the ATH8 cells. The ATH8 assay is described in the following reference: Matsukura, pages 285–304 in Antisense RNA and DNA (Wiley-Liss, New York, 1992).

Figure 3:
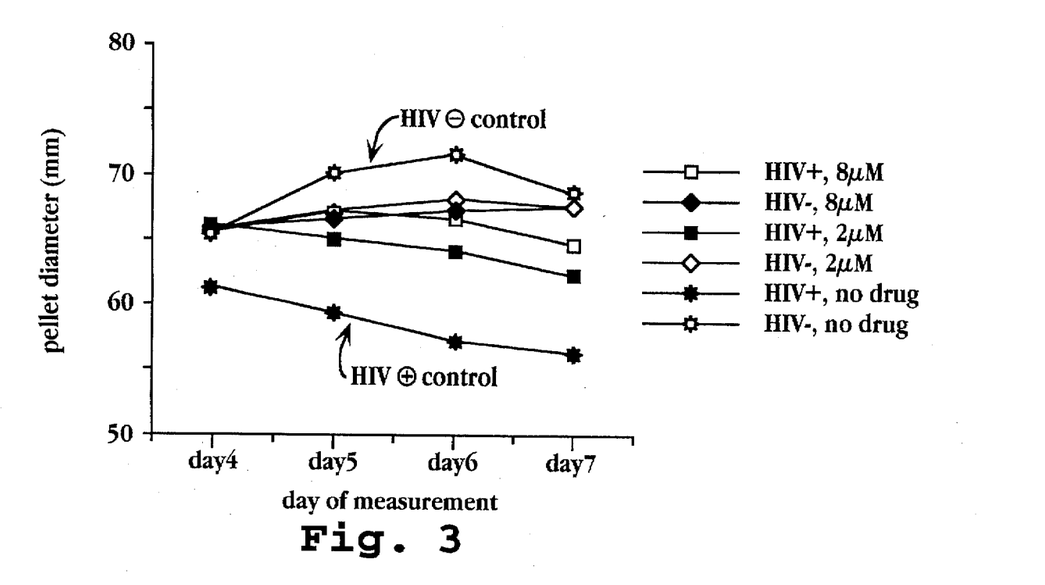
FIG. 3 illustrates the results of the inhibition of the cytotoxic effects of HIV in an ATH8 cell assay.

The cytopathic effect examined in the assay was the lytic effect of HIV and/or drug on the ATH8 cells. A measure of the degree of viral activity is the degree to which cells are lysed at the end of a given time period in culture. Protection against lysis is measured by the size of pellet formed after cells are harvested from culture and centrifuged, as described in the references cited above. The results of the assays are summarized in Table II and FIGS. 3a and 3b.

TABLE II

| Oligo-nucleotide Clamp | Inhibition of Cytotoxic* Effects at 2 mM Concentration | Inhibition of Cytotoxic* Effects at 8 mM Concentration | Toxicity** |
|---|---|---|---|
| 015 | 0 | 0 | 0 |
| 014 | +++ | +++ | 0 |
| 013 | ++ | ++ | 0 |
| 021 | ++ | ++ | 0 |
| 022 | ++ | – | + |
| 023 | ++ | – | + |
| 050A | ++ | ++ | 0 |
| 050B | ++ | – | + |
| 051 | +++ | – | + |
| 052A | ++ | +++ | 0 |
| 052B | not tested | – | + |
| 053 | + | + | 0 |

*"0" indicates no inhibitory effect observed; number of +'s indicates relative inhibitory effect; "–" indicates toxicity at that dose.
**"0" indicates no toxicity observed; "+" indicates some toxicity observed.

FIG. 3 shows the change in pellet size versus time under different experimental conditions for oligonucleotide clamp 014. Curves 1 and 2 illustrate results from positive and negative controls, i.e. curve 1 illustrates the results for uninfected ATH8 cells without drug (negative control) and curve 2 illustrates the results for infected ATH8 cells without drug (positive control). Curves 3 and 4 illustrate results from cultures containing 8 μM of oligonucleotide clamp in infected and uninfected ATH8 cells, respectively. Curves 5 and 6 illustrate results from cultures containing 2 μM of oligonucleotide clamp in infected and uninfected ATH8 cells, respectively. FIG. 3 shows that clamp 014 has a clear and positive effect at both concentrations without toxicity.

EXAMPLE 3

Synthesis of Two-component Oligonucleotide Clamps with Cholesterol Binding Moieties The following two-component oligonucleotide clamps were synthesized by the procedures described above and tested in the ATH8 assay described above:

5'-Chol-CACTTTTCTTTTGGGGGGTCA-3'
3'-Chol-ACTTTTCTTTTCCCCCCTCAC-5'
(DL033/DL034)
5'-Chol-CACTTTTCTTTTGGGGGGTCA-Chol-3'
3'-Chol-ACTTTTCTTTTCCCCCCTCAC-Chol-5'

EXAMPLE 4

Synthesis of Oligonucleotide Clamps with Phosphorothioate Linkages

The following oligonucleotide clamps containing phosphorothioate linkages were synthesized by the procedures described above and tested in the ATH8 assay described above:

5'-Chol-CpsApsCps(Tps)₄Cps(Tps)₄(Gps)₆CpsApsCpsAps-CpsTps(Cps)₆(Tps)₄Cps(Tps)₄CpsAps-Chol-3'
066

5'-Chol-CACTTTTCTTTTGGGGGGT-3'
3'-Chol-ApsCps(Tps)₄Cps(Tps)₄(Gps)₆T-5'
067/DL033 wherein "ps" indicates the presence of a phosphorothioate linkage.

EXAMPLE 5

Synthesis of Oligonucleotide Clamp with Cholesterol Binding Moieties and a Polyethylene Glycol Hinge Region The following oligonucleotide clamp having a non-nucleosidic hinge region is synthesized as described above and employing the protected ethyl glycol phosphoramidites disclosed by Durand et at Nucleic Acids Research, 18: 6353–6359 (1990); and Rumney et al (cited above):

5'-Chol-CACTTTTCTTTTGGGGGG$_p$(OCH₂CH₂)$_{5p}$TCCCCCCTTTTCTTTTCA-Chol-3' wherein "p" indicates the presence of a phosphodiester linkage.

3'-bromoacetylamino oligonucleotides were prepared similarly to their 5' counterparts, except that a 3'-amino-oligonucleotide precursor was employed. The 3' phosphorothioate oligonucleotide is formed as described above.

5'-CACTGGGGGGTTTTGTTTTGTTTTCA(CH₂)₆NHC(=O)CH₂Br
5'-ACTCCCCCCTTTTCTTTTCAP(=O)(O⁻)S
064/063

5'-CACTGGGGGGTTTTCA(3')-X-(3')ACTTTTCTTTTCCCCCCTCA-5'
064/063* wherein X is —(CH₂)₆NHC(=O)CH₂P(=O)(O⁻)S—.

5'-Chol-CACTGGGGGGTTTTGTTTTCA(3')-X-(3')ACTTTTCTTTTCCCCCCTCA-Chol-5'
064/063**

EXAMPLE 6

Synthesis of Oligonucleotide Clamp having Bromoacetyl/phosphorothioate Binding Moieties The following oligonucleotide clamp is synthesized by the procedures described above and tested in the ATH8 assay:

5'-BrCH₂C(=O)NH—CACTTTTCTTTTGGGGGGTCA-Chol-3'
3'-SP(=O)(O⁻)ACTTTTCTTTTCCCCCCTCAC-Chol-5'
BrAc033/PS034

5'-bromoacetylamino oligonucleotides are prepared as follows: 15 μL of 0.4M N-succinimidyl bromoacetate (e.g. Calbiochem) in N,N-dimethylformamide (DMF) is added to 4.9 A$_{260}$ units of a 5'-amino-oligonucleotide precursor in 10 mL of 0.2M sodium borate buffer at room temperature. After about 35 minutes the mixture is diluted (0.5 mL H₂O), desalted by gel filtration on a NAP-5 column (Pharmacia), purified by reverse phase HPLC (as described below), and again desalted to yield 4 A$_{260}$ units of 5'-bromoacetylamino oligonucleotide (elution time for reverse phase HPLC, 17.4 minutes; ion exchange HPLC, 17.4 minutes). Ion exchange HPLC is carried out on a Dionex Omni Pak NA100 4×250 mm column at pH 12 (0.001M NaOH) with a 2%/minute gradient of 1.0M NaCl in 0.01M NaOH. Reverse phase HPLC is carried out on a Hypersil ODS 4.6×200 mm column with a 1%/minute gradient of acetonitrile in 0.03M triethylammonium acetate buffer, pH 7.0. A 5'-amino-oligonucleotide is prepared as described above. The 3' phosphorothioate oligonucleotide is formed as described above.

EXAMPLE 7

Synthesis of Oligonucleotide Clamps Consisting of Two Oligonucleotide Moieties in Opposite Orientations with respect to Hinge Region and/or Binding Moieties The following oligonucleotide clamps were prepared by the procedures described above and as noted below. The wherein X is phosphodiester. All three clamps were tested in the ATH8 assays described above.

EXAMPLE 8

Synthesis of Oligonucleotide Clamp Carrying a Fluorescent Label Attached to Hinge Region The following oligonucleotide clamp is synthesized as described above:

5'-Chol-CACTTTTCTTTTGGGGGGCA$_p$X$_p$ACTC-CCCCCTTTTCTTTTCA-Chol-3' wherein "pXp" indicates the presence of a branching linkage or base, e.g. a phosphoramidate linkage, and amino derivatized cytidine, or the like. A phosphoramidate linkage is introduced by carrying out the coupling of one nucleoside as a hydrogen phosphonate monomer then oxidizing the resulting phosphite linkage with I₂ and an alkyldiamine, e.g. a hexyldiamine as taught by Agrawal et al, Nucleic Acids Research, 18: 5419–5423 (1990); and Jager et al, Biochemistry, 27: 7237–7246 (1988). This results in a free amine that can be reacted with an activated dye.

Preferably, an AminoModifier E branching linkage (DMT-O-CH₂CH(CH₂NH-Fmoc)-O-phosphoramidite) (commercially available from Clontech Laboratories, Palo Alto) is introduced into the hinge region. After deprotection and cleavage a free primary amino group is available as an attachment site for a variety of activated fluorescent dyes, e.g. the NHS esters of fluorescein or rhodamine, commercially available from Applied Biosystems (Foster City, Calif.) as TAMRA-NHS, FAM-NHS, ROX-NHS, and JOE-NHS.

EXAMPLE 9

Synthesis of Oligonucleotide Clamp Carrying a Oligonucleotide Attached to Hinge Region The oligonucleotide clamp of Example 8 is synthesized with the free primary amine in its hinge region. The amine is derivatized with bromoacetyl as described above. Separately, an oligonucleotide is prepared having either a 3' or 5' monophosphorothioate group, as desired. The bromoacetylated clamp and the oligonucleotide are combined in an aqueous solution and frozen as described above.

ester linkage. After purification d, e, and f are combined in solution and frozen as described above. The oligonucleotide clamp dimer is then purified by gel electrophoresis.

EXAMPLE 10

Synthesis of Oligonucleotide Clamp Dimer

The two oligonucleotide clamps shown below having free amines in their hinge regions are separately synthesized and bromoacetylated as described in Example 2. In a third synthesis, an oligonucleotide, or other linear polymeric unit, is prepared which has a monophosphorothioate group at both its 5' and 3' ends.

5'-Chol-CACTTTTCMeTTTTCCCCCCTCAC(pnp)ACTCC-CCCCTTTTCTTTTAC(3')-Chol
d
5'-Chol-TTTTTTTTTTTTCAC(pnp)ACTTTTTTTTTTTT(3')-Chol
e f wherein "pnp" represents a linkage or monomer containing an bromoacetylamino functionality and "p" is a phosphodi-

---

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 16 nucleotides
( B ) TYPE: nucleic acid
( C ) STRANDEDNESS: single
( D ) TOPOLOGY: linear ( x i ) SEQUENCE DESCRIPTION: SEQ ID NO: 1:

AAAAGAAAAG GGGGGA     16

( 2 ) INFORMATION FOR SEQ ID NO: 2:

( i ) SEQUENCE CHARACTERISTICS:
( A ) LENGTH: 42 nucleotides
( B ) TYPE: nucleic acid
( C ) STRANDEDNESS: single
( D ) TOPOLOGY: linear ( x i ) SEQUENCE DESCRIPTION: SEQ ID NO: 2:

CACTTTTCTT TTCCCCCCTC ACACTCCCCC CTTTTCTTTT AC     42

( 2 ) INFORMATION FOR SEQ ID NO: 3:

( i ) SEQUENCE CHARACTERISTICS:
( A ) LENGTH: 42 nucleotides
( B ) TYPE: nucleic acid
( C ) STRANDEDNESS: single
( D ) TOPOLOGY: linear ( x i ) SEQUENCE DESCRIPTION: SEQ ID NO: 3:

CACTTTTCTT TTGGGGGGTC ACACTCCCCC CTTTTCTTTT AC     42

( 2 ) INFORMATION FOR SEQ ID NO: 4:

```
( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TTTCTTTTC  ACACTTTCT  TTTGGGGGT  CACACTCCCC  CC                    4 2

( 2 ) INFORMATION FOR SEQ ID NO: 5:

( i ) SEQUENCE CHARACTERISTICS:
            ( A ) LENGTH: 15 nucleotides
            ( B ) TYPE: nucleic acid
            ( C ) STRANDEDNESS: single
            ( D ) TOPOLOGY: linear ( x i ) SEQUENCE DESCRIPTION: SEQ ID NO: 5:

TTTTTTTTT  TTCAC                                                    1 5

( 2 ) INFORMATION FOR SEQ ID NO: 6:

( i ) SEQUENCE CHARACTERISTICS:
            ( A ) LENGTH: 16 nucleotides
            ( B ) TYPE: nucleic acid
            ( C ) STRANDEDNESS: single
            ( D ) TOPOLOGY: linear ( x i ) SEQUENCE DESCRIPTION: SEQ ID NO: 6:

ACTTTTTTTTT  TTTT                                                   1 6
```

I claim:

1. The oligonucleotide clamp for specifically binding to a target polynucleotide, the oligonucleotide clamp comprising:

(a) at least one oligonucleotide moiety containing a polynucleotide sequence capable of specifically binding to a target polynucleotide; and (b) one or more pairs of binding moieties attached covalently to said oligonucleotide, each pair of binding moieties comprising a first binding moiety and a second binding moiety, whereby specific binding of said oligonucleotide moiety to the target polynucleotide is effective to place said first and second bonding moieties in proximity to each other, such that a stable covalent or non-covalent linkage is formed between the first binding moiety and the second binding moiety, producing a macrocyclic oligonucleotide clamp structure bound to said target polynucleotide, further comprising two oligonucleotide moieties defined by the formulas:

X—oligo1—W and

Y—oligo2—Z wherein:

X—oligo1—W and Y—oligo2—Z are oligonucleotides which are each specific for either a first polynucleotide sequence in said target polynucleotide or a complementary sequence thereof;

X and Y are a first pair of binding moieties such that X and Y form a stable covalent or non-covalent linkage whenever X and Y are brought in proximity with each other as a result of specific binding of said oligonucleotide moieties to the target polynucleotide; and W and Z are a second pair of binding moieties such that W and Z form a stable covalent or non-covalent linkage whenever W and Z are brought in proximity with each other as a result of specific binding of said oligonucleotide moieties to the target polynucleotide, whereby a macrocyclic oligonucleotide clamp structure is formed between X—oligo1—W and Y—oligo2—Z.

2. The oligonucleotide clamp of claim 1 wherein oligo1 and oligo2 have the same length and are from about 6 to about 40 nucleotides in length.

3. The oligonucleotide clamp of claim 2 wherein one or both of either X and Y or W and Z form a hydrophobic complex when said oligonucleotide moieties are bound to the target polynucleotide.

4. The oligonucletide clamp of claim 3 wherein X and Y are selected from the group consisting of alkanes, fatty acids, fatty alcohols, steroids, waxes, and fat-soluble vitamins.

5. The oligonucleotide clamp of claim 4 wherein X and Y are each a perhydrocyclopentanophenanthrene having from 19 to 30 carbon atoms and from 0 to 6 oxygen atoms.

6. The oligonucleotide clamp of claim 5 wherein X and Y are each cholesterol.

7. The oligonucleotide clamp of claim 4 wherein X, Y, W, and Z are selected from the group consisting of alkanes, fatty acids, fatty alcohols, steroids, waxes, and fat-soluble vitamins.

8. The oligonucleotide clamp of claim 7 wherein X, Y, W, and Z are cholesterol.

9. The oligonucleotide clamp of claim 2 wherein either one or both of X and Y or W and Z form a covalent linkage when said oligonucleotide moieties are bound to the target polynucleotide.

10. The oligonucleotide clamp of claim 9 wherein X is selected from the group consisting of phosphorothioate and phosphorodithioate and wherein Y is selected from the group consisting of haloacyl- or haloalkylamino.

11. The oligonucleotide clamp of claim 10 wherein X and Y are thiophosphoryl.

12. The oligonucleotide clamp of claim 10 wherein W and Z are cholesterol.

13. A kit for detecting a target polyneotide, the kit comprising a hybridization buffer and an oligonucleotide clamp specific for the target polynucleotide, the oligonucleotide clamp having a signal generation moiety for generating a detectable signal in the presence of the target polynucleotide, said oligonucleotide clamp further comprising two oligonucleotide moieties defined by the formulas:

X—oligo1—W and

Y—oligo2—Z wherein:

X—oligo1—W and Y—oligo2—Z are oligonucleotides which are each specific for either a first polynucleotide sequence in said target polynucleotide or a complementary sequence thereof;

X and Y are a first pair of binding moieties such that X and Y form a stable covalent or non-covalent linkage whenever X and Y are brought in proximity with each other as a result of specific binding of said oligonucleotide moieties to the target polynucleotide; and W and Z are a second pair of binding moieties such that W and Z form a stable covalent or non-covalent linkage whenever W and Z are brought in proximity with each other as a result of specific binding of said oligonucleotide moieties to the target polynucleotide, whereby a macrocyclic oligonucleotide clamp structure is formed between X—oligo1—W and Y—oligo2—Z.

(a) at least one oligonucleotide moiety containing a polynucleotide sequence capable of specifically binding to a target polynucleotide; and (b) one or more pairs of binding moieties attached covalently to said oligonucleotide, each pair comprising a first binding moiety and a second binding moiety, whereby specific binding of said oligonucleotide moiety to such a target polynucleotide is effective to place said first and second bonding moieties in proximity to each other, such that a stable covalent or non-covalent linkage is formed between the first binding moiety and the second binding moiety, producing a macrocyclic oligonucleotide clamp structure bound to said target polynucleotide.

14. The kit of claim 13 wherein oligo1 and oligo2 have the same length and are from about 6 to about 40 nucleotides in length.

15. The kit of claim 14 wherein one or both of either X and Y or W and Z form a hydrophobic complex when said oligonucleotide moieties are bound to the target polynucleotide.

16. The kit of claim 15 wherein X and Y are selected from the group consisting of alkanes, fatty acids, fatty alcohols, steroids, waxes, and fat-soluble vitamins.

17. The kit of claim 16 wherein X and Y are each a perhydrocyclopentanophenanthrene having from 19 to 30 carbon atoms and from 0 to 6 oxygen atoms.

18. The kit of claim 17 wherein X and Y are each cholesterol.

19. The kit of claim 16 wherein X, Y, W, and Z are each selected from the group consisting of alkanes, fatty acids, fatty alcohols, steroids, waxes, and fat-soluble vitamins.

20. The kit of claim 19 wherein X, Y, W, and Z are cholesterol.

21. The kit of claim 14 wherein either one or both of X and Y or W and Z form a covalent linkage when said oligonucleotide moieties are bound to the target polynucleotide.

22. The kit of claim 21 wherein X is selected from the group consisting of phosphorothioate and phosphorodithioate and wherein Y is selected from the group consisting of haloacyl- or haloakyl-amino.

23. The kit of claim 22 wherein X and Y are thiophosphoryl.

24. The kit of claim 22 wherein W and Z are cholesterol.

* * * * *